(12) United States Patent
Lei et al.

(10) Patent No.: US 9,006,439 B2
(45) Date of Patent: Apr. 14, 2015

(54) CAMPTOTHECIN DERIVATIVES HAVING ANTI-TUMOR ACTIVITY

(75) Inventors: Xiaoguang Lei, Beijing (CN); Xiuguo Zhang, Beijing (CN)

(73) Assignee: Ningbo Team Pharmaceutical Co., Ltd (CN)

( * ) Notice: Subject to any disclaimer, the term of this patent is extended or adjusted under 35 U.S.C. 154(b) by 0 days.

(21) Appl. No.: 14/006,102

(22) PCT Filed: Apr. 6, 2012

(86) PCT No.: PCT/CN2012/073578
§ 371 (c)(1),
(2), (4) Date: Sep. 18, 2013

(87) PCT Pub. No.: WO2012/136144
PCT Pub. Date: Oct. 11, 2012

(65) Prior Publication Data
US 2014/0011833 A1      Jan. 9, 2014

(30) Foreign Application Priority Data

Apr. 7, 2011 (CN) .......................... 2011 1 0086102

(51) Int. Cl.
| C07D 491/22 | (2006.01) |
| A61K 31/475 | (2006.01) |
| A61K 31/4745 | (2006.01) |
| A61K 9/20 | (2006.01) |
| A61K 9/48 | (2006.01) |

(52) U.S. Cl.
CPC .......... *C07D 491/22* (2013.01); *A61K 31/4745* (2013.01); *A61K 9/2018* (2013.01); *A61K 9/2054* (2013.01); *A61K 9/4866* (2013.01)

(58) Field of Classification Search
CPC ............................ C07D 491/22; A61K 31/475
USPC .............................................. 514/283; 546/48
See application file for complete search history.

(56) References Cited

U.S. PATENT DOCUMENTS

| 7,105,492 B2 * | 9/2006 | Dallavalle et al. .............. 514/25 |
| 2009/0325996 A1 * | 12/2009 | Lu et al. ........................ 514/283 |

FOREIGN PATENT DOCUMENTS

| CN | 1616460 A | 5/2005 |
| CN | 101407516 A | 4/2009 |
| CN | 102731516 | 7/2014 |

OTHER PUBLICATIONS

Chinese Office Action, Oct. 10, 2012, for Ningbo Team Pharmaceutical Co., Ltd, Chinese Application No. 201110086102.6.
International Search Report, Jul. 5, 2012, for International Application No. PCT/CN2012/073578.
Written Opinion, Jun. 26, 2012, for International Application No. PCT/CN2012/073578.

* cited by examiner

*Primary Examiner* — John Mabry
*Assistant Examiner* — Daniel Carcanague
(74) *Attorney, Agent, or Firm* — Law Offices of Albert Wai-Kit Chan, PLLC

(57) ABSTRACT

Disclosed are novel camptothecin derivatives having anti-tumor activity (the basic structure thereof is as shown in the figure) and compositions of such compounds and use thereof. The compounds according to the present invention exhibit very good water solubility and stability, show good selectivity among drugs of the same category, and have a very high therapeutic index. Such compounds are promising as therapeutic agents for treating tumors.

5 Claims, 3 Drawing Sheets

CAMPTOTHECIN DERIVATIVES HAVING ANTI-TUMOR ACTIVITY

CROSS-REFERENCE TO RELATED APPLICATIONS

This application is the National Stage of International Application No. PCT/CN2012/073578, filed Apr. 6, 2012, which claims priority of Chinese Application No. 201110086102.6, filed Apr. 7, 2011. The entire disclosures of the preceding applications are hereby incorporated by reference into this application.

FIELD OF THE INVENTION

This invention relates to compounds for anti-tumor drug, particularly to a kind of camptothecin derivatives with novel chemical structure and high anti-tumor activity, their synthesis and uses.

BACKGROUND OF THE INVENTION

Cancerous tumors are currently one of the most severe diseases that endanger the lives and health of the world population. According to the World Health Organization (WHO), statistics show that there are 16 million incidences of cancer in the world each year causing the death of about 600 million people and is the second leading cause of death ranked only under cardiovascular diseases. There are more than 70 types of anti-tumor drugs marketed worldwide in total and the number is rapidly growing at 1-2 new drugs per year. However, in China, the development of anti-tumor drugs is still at an infancy stage; for economic and supply reasons, majority of tumor patients still do not receive treatment with advanced drugs. The development of novel anti-tumor drugs with autonomous intellectual property rights is therefore of great significance to the country's developments in economy and healthcare. Camptothecin (CPT) is a kind of alkaloid isolated from Camptotheca acuminata of the Nyssaceae Family. It acts to inhibit DNA topoisomerase I. Due to its low specificity, camptothecin results in hematuria and bone marrow suppression which limit its further application. Semi-synthetic camptothecin derivatives, after structural modification, have increased specificity, lower toxicity, and improved efficacy. Currently, camptothecin drugs available in both domestic and foreign markets include irinotecan (CPT-11), topotecan, 10-hydroxy camptothecin and belotecan (CKD-602) which became available in 2004. Other camptothecin drugs which have undergone clinical trials include NP-1350 (karenitecin), gimatecan, chimmitecan, etc.

Irinotecan is the most successful camptothecin derivative resulting from structural modification. It has broad-spectrum anti-tumor effects and, since 5-fluorouracil 40 years ago, is the only first-line drug to be used for treatment of metastatic colorectal cancer while also being used in treatment of lung cancer, ovarian cancer, breast cancer, stomach cancer and pancreatic cancer. Topotecan is the worst camptothecin derivative resulting from structural modification. Preclinical evaluation shows that it is ineffective for most tumors and, clinically, it could only be used for treating small cell lung cancer which is known to be most responsive to chemotherapy. Even so, the remission time is short and the effect is poor.

Camptothecin is a pentacyclic alkaloid which is amenable to a variety of structural modifications at the C-7, 9- and 20 positions. Highly efficacious compounds of low toxicity can be obtained when structural modifications are made at the C-7 and 9 positions. For examples, ethyl group was introduced to irinotecan at C-7; N-t-butyloxymethyloxime group was introduced to gimatecan at C-7; said group is lipophilic and can pass through the blood brain barrier. Gimatecan is undergoing clinical trials for treatment of glioma. Chimmitecan, with propenyl group introduced at C-9, also has good anti-tumor effect. However, topotecan, with dimethylaminomethyl introduced at C-9, did not demonstrate an increase in efficacy and reduced toxicity, and in fact, its toxicity increased in comparison to 10-OH-CPT. The only improvement was its solubility. Therefore, any improvement in activity of the compounds by the introduction of chemical groups at C-7 or C-9 positions is determined by the nature of the group that is introduced.

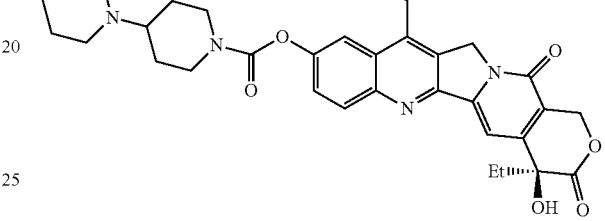

CPT-11

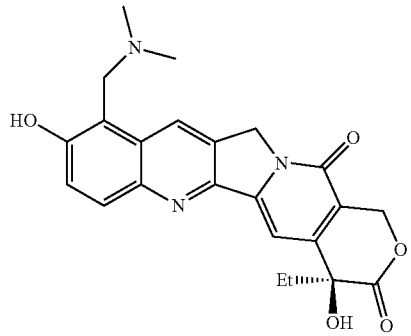

Topotecan

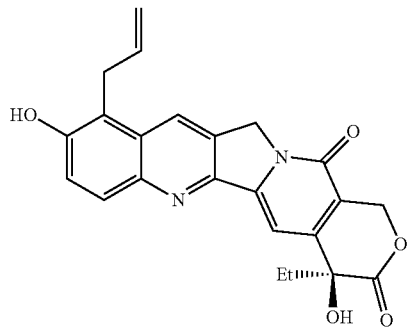

Chimmitecan

-continued

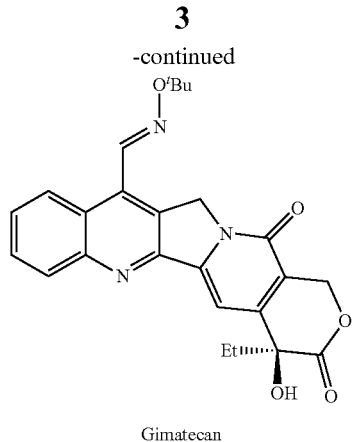
Gimatecan

SUMMARY OF THE INVENTION

The inventors of the present invention have conducted detailed systematic study on the camptothecin anti-tumor drugs and, after selection via long-term experimentations, discovered that compounds obtained by the introduction of oxime or other nitrogen-containing olefinic groups at C-9 together with the introduction of functional groups such as hydroxyl or their derivatives at C-10 or C-11 [Structural Formula (1) in Summary of Invention] showed excellent anti-tumor activity with significant increase in anti-tumor effect in vivo. These compounds are among the most specific new camptothecin derivatives and demonstrate the prospect of developing anti-tumor drugs based on this kind of compounds, which have not been reported in China and represent novel compounds of the present invention.

DETAILED DESCRIPTION OF THE INVENTION

Figure 1:
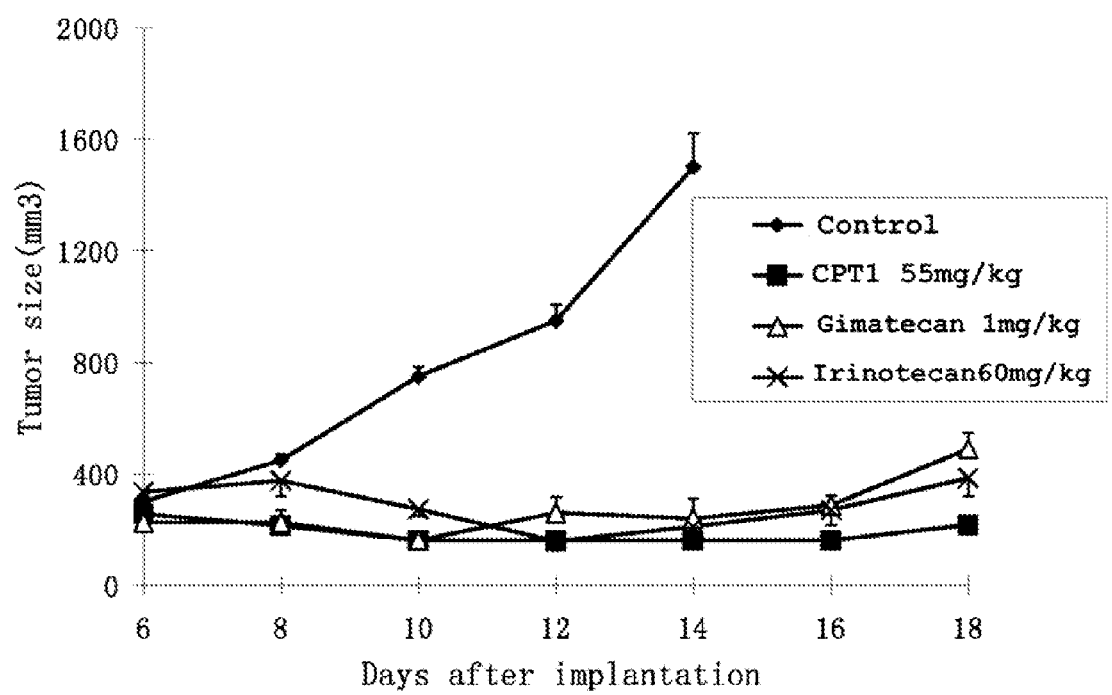
FIG. 1: Comparison of the anti-tumor effects of CPT1, Gemma topotecan and irinotecan on BX-PC3 human pancreatic cancer (iv, inj. q2dx4).
Figure 2:
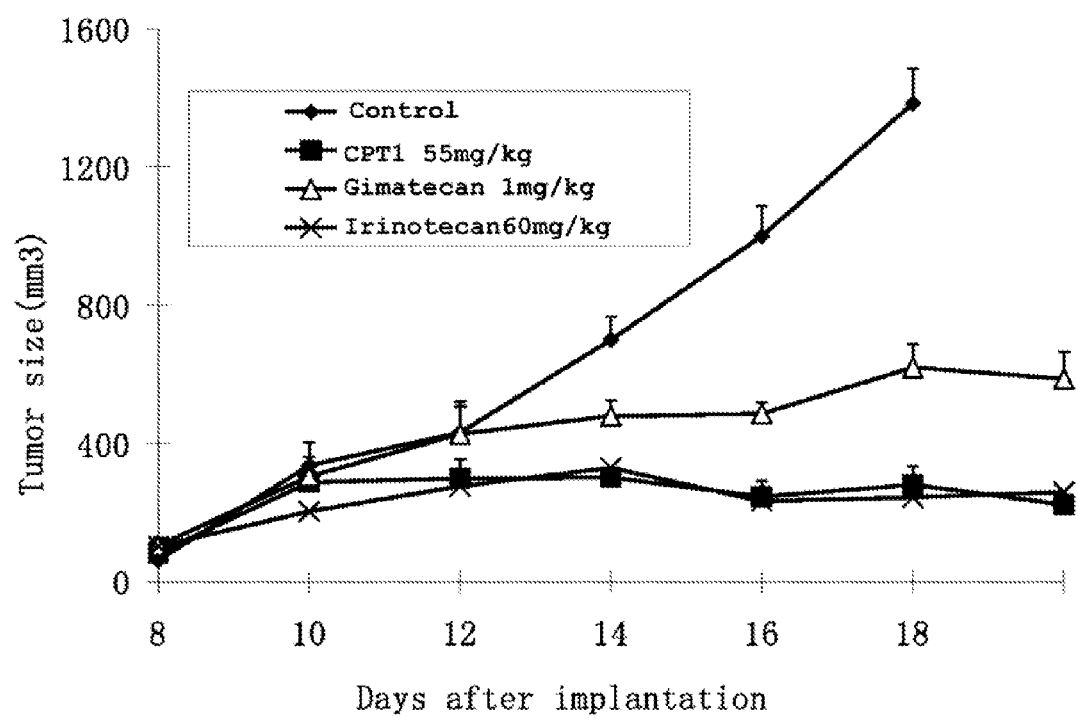
FIG. 2: Comparison of the anti-tumor effects of CPT1, Gemma topotecan and irinotecan on NT-29 human colon cancer (iv, inj. q2dx4).
Figure 3:
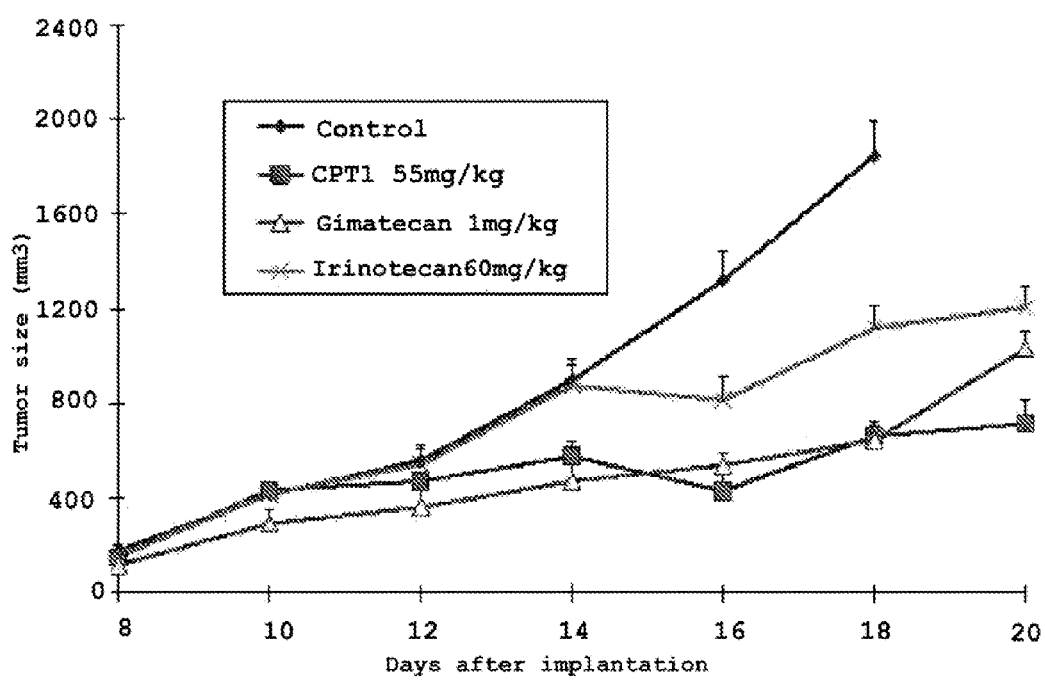
FIG. 3: Comparison of the anti-tumor effects of CPT1, Gemma topotecan and irinotecan on A549 human non-small cell lung cancer (iv, inj. q2dx4).

The present invention provides:
Novel camptothecin derivatives with anti-tumor activity, compounds of said camptothecin derivatives and their pharmaceutical compositions, and uses of said compounds and the preparation of their compositions in the treatment of cancer.

1. The Basic Chemical Structure of the New Camptothecin Derivatives is as Follows:

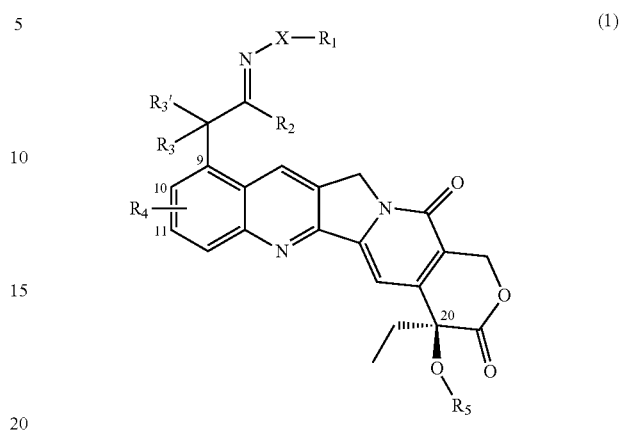

In the above structural formula:

$R_1$ represents H; straight-chain, branched-chain or cyclic $C_1$-$C_{10}$ alkyl group; straight-chain, branched-chain or cyclic $C_1$-$C_{10}$ alkyl group substituted with F; straight-chain, branched-chain or cyclic $C_1$-$C_{10}$ acyl group; straight-chain, branched-chain or cyclic $C_1$-$C_{10}$ acyl group substituted with F; $C_6$-$C_{18}$-carbon aromatic ring of; $C_6$-$C_{18}$ carbon aromatic ring substituted with halogen (F, Cl, Br, I), nitro ($NO_2$), hydroxyl (OH), amino ($NH_2$), cyano (CN); aromatic ring comprising heteroatom (N, O, S);

X represents O; NH; $NR_6$; $R_6$ represents straight-chain, branched-chain or cyclic $C_1$-$C_{10}$ alkyl group; straight-chain, branched-chain or cyclic $C_1$-$C_{10}$ alkyl group substituted with F; straight-chain, branched-chain or cyclic $C_1$-$C_{10}$ acyl group; straight-chain, branched-chain or cyclic $C_1$-$C_{10}$ acyl group substituted with F;

$R_2$ represents H; straight-chain, branched-chain or cyclic $C_1$-$C_{10}$ alkyl group; straight-chain, branched-chain or cyclic $C_1$-$C_{10}$ alkyl group substituted with F; $R_3$ and $R_3'$ represent the same or not the same group, which can be H; F; straight-chain, branched-chain or cyclic $C_1$-$C_{10}$ alkyl group; straight-chain, branched-chain or cyclic $C_1$-$C_{10}$ alkyl group substituted with F;

$R_4$ represents the same or not the same group at the $C_{10}$ and $C_{11}$ positions, which can be halogen (F, Cl, Br, I); nitro ($NO_2$); hydroxyl (OH); amino ($NH_2$); straight-chain, branched-chain or cyclic $C_1$-$C_{10}$ alkyl group; straight-chain, branched-chain or cyclic $C_1$-$C_{10}$ alkyl group substituted with F; straight-chain, branched-chain or cyclic $C_1$-$C_{10}$ acyl group; straight-chain, branched-chain or cyclic $C_1$-$C_{10}$ acyl group substituted with F; or $R_4$ represents $OR_7$ at position $C_{10}$ or $C_{11}$; wherein $R_7$ represents straight-chain, branched-chain or cyclic $C_1$-$C_{10}$ carbonyl group; straight-chain, branched-chain or cyclic $C_1$-$C_{10}$ carbonyl group substituted with F; straight-chain, branched-chain or cyclic $C_1$-$C_{20}$ carbonyl group containing N atom; carbonyl group containing natural or non-natural amino acids and C-terminal peptides composed of said amino acids;

$R_5$ represents H; straight-chain, branched-chain or cyclic $C_1$-$C_{10}$ carbonyl group; straight chain, branched-chain or cyclic $C_1$-$C_{10}$ carbonyl group substituted with F; straight-chain, branched-chain or cyclic $C_1$-$C_{20}$ carbonyl group containing N atom; carbonyl group containing natural or non-natural amino acids and C-terminal peptides composed of said amino acids.

Pharmaceutically acceptable salts of the above-mentioned compounds are characteristically formed by the basic amine group in (4'-piperidinylpiperidinyl) carbonyloxy or an amino group in a natural or non-natural amino acid reacting with medical grade inorganic or organic acids. These salts make the drugs soluble in water. For example: hydrochlorides, hydrobromides, phosphates, sulfates, acetates, trifluoroacetates, citrates, maleates, oxalates, succinates, benzoates, tartrates, fumarates, mandelates, ascorbates, malates, methanesulfonates, p-toluenesulfonates, etc.

The preferred embodiments of this invention are the following compounds (CPT1-CPT10):

CPT1: 9-t-butyloxyethyloxime-10-[(4'-piperidinylpiperidinyl) carbonyloxy]-camptothecin;

CPT2: 9-t-butyloxyethyloxime-10-hydroxy-camptothecin;

CPT3: 9-t-butyloxyethyloxime-10-fluoro-camptothecin;

CPT4: 9-t-butyloxyethyloxime-10-phenylalanine-carbonyloxy-camptothecin;

CPT5: 9-methoxyethyloxime-10-[(4'-piperidinylpiperidinyl) carbonyloxy]-camptothecin;

CPT6: 9-phenylaminoethylhydrazone-10-[(4'-piperidinylpiperidinyl)carbonyloxy]-camptothecin;

CPT7: 9-t-butyloxyethyloxime-camptothecin;

CPT8: 9-t-butyloxyethyloxime-10-acetoxy]-camptothecin;

CPT9: 9-t-butyloxyethyloxime-10-[(4'-piperidinylpiperidinyl) carbonyloxy]-20-phenylalanine carbonyloxy-camptothecin;

CPT10: 9-t-butyloxyethyloxime-20-phenylalanine-carbonyloxy-camptothecin.

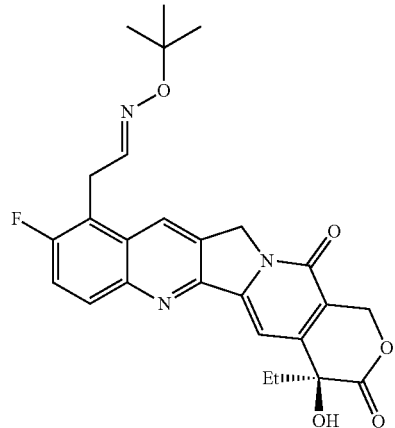

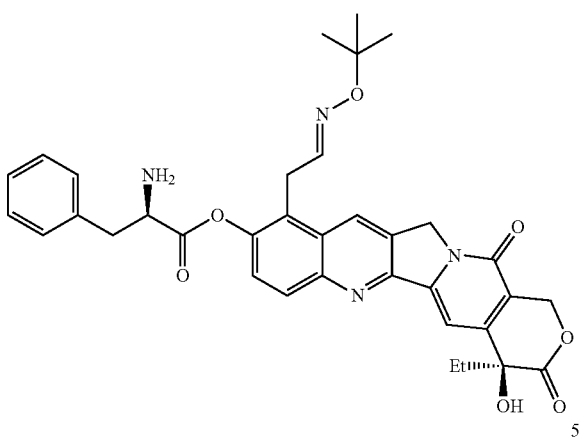

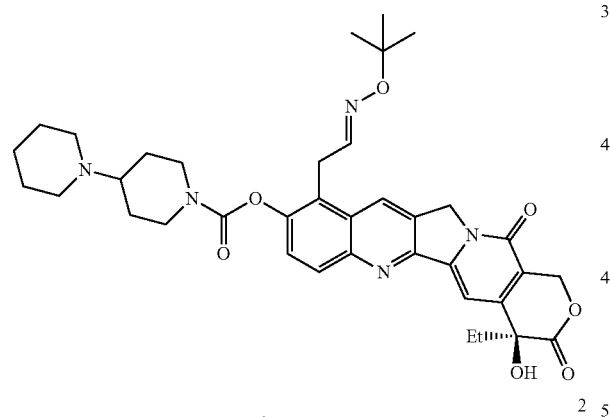

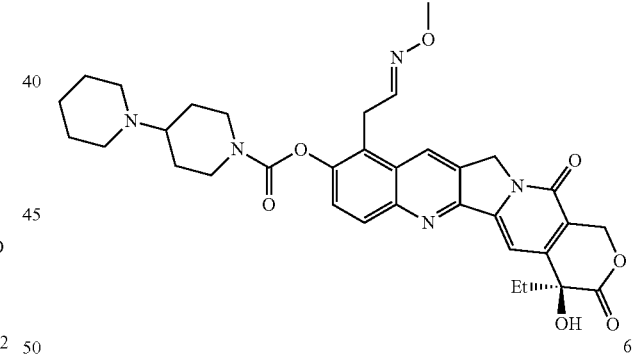

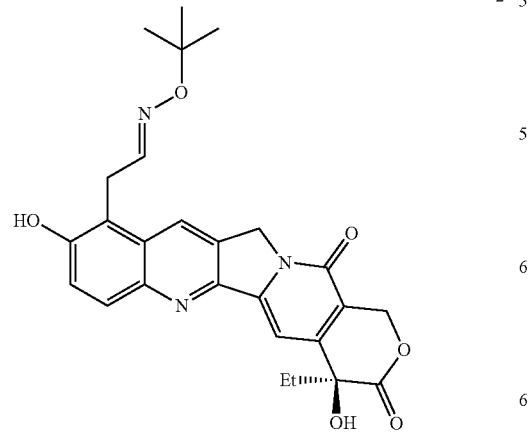

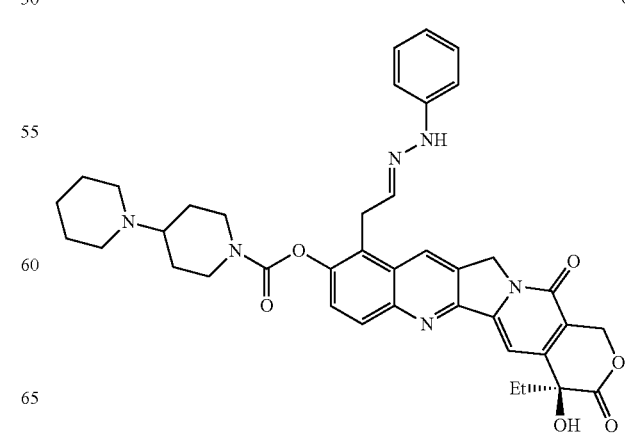

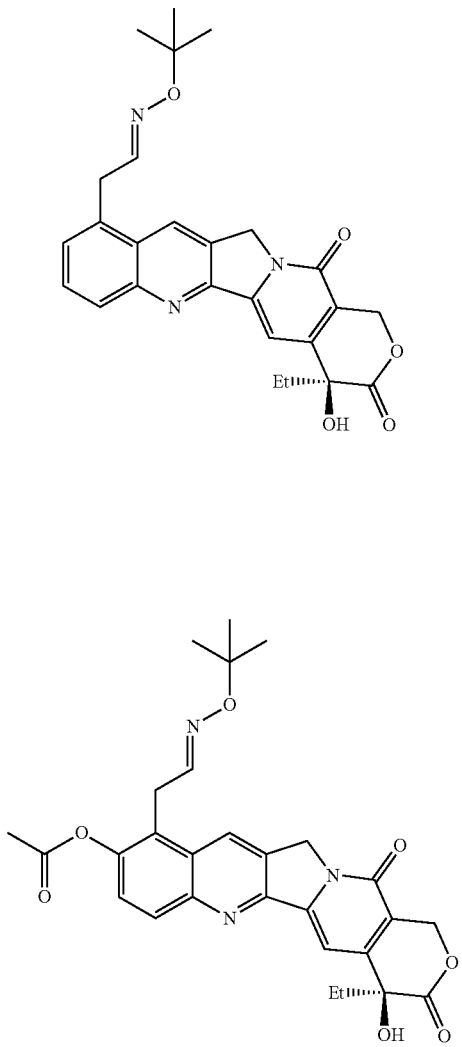
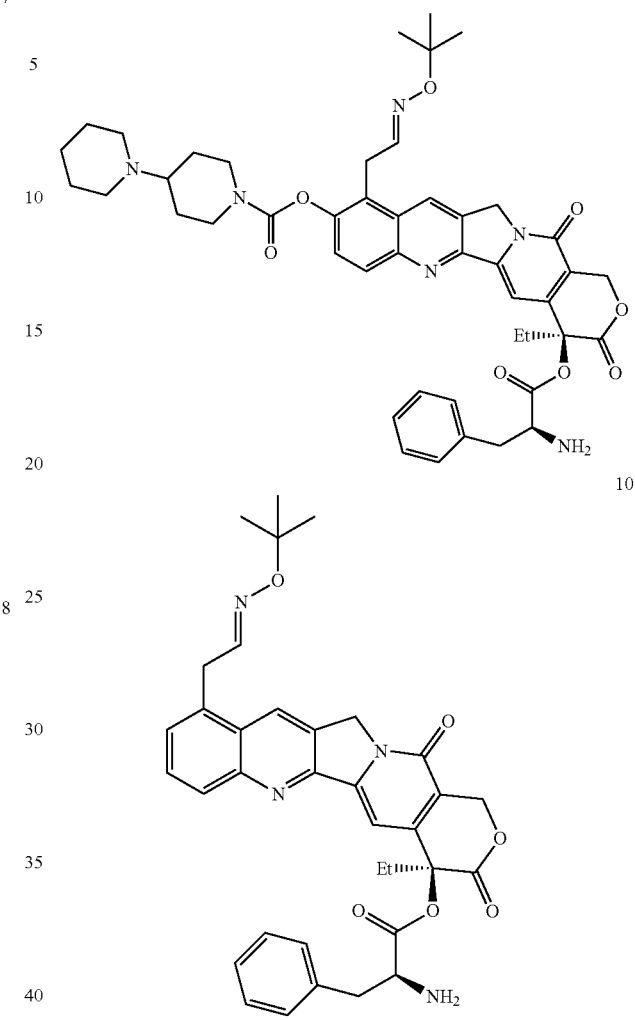
This invention also provides the methods for preparation of the representative compounds of this invention as shown in the below diagram:
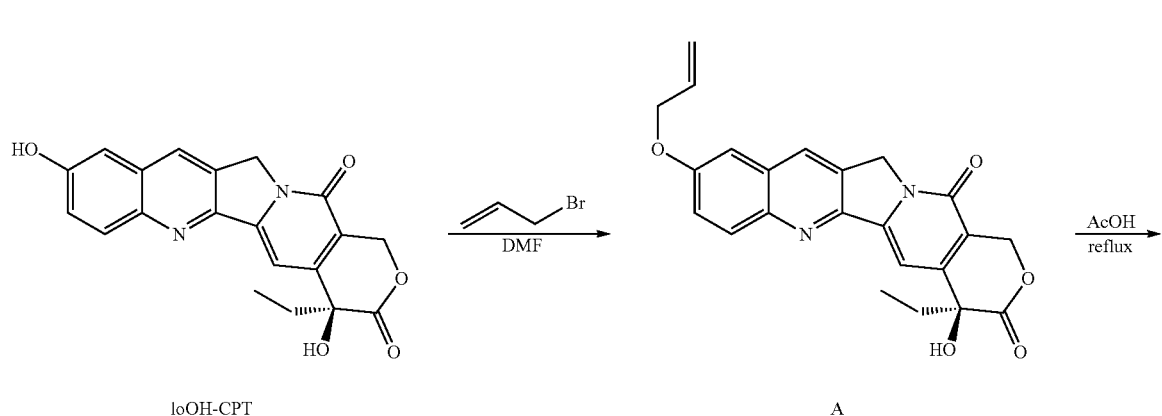

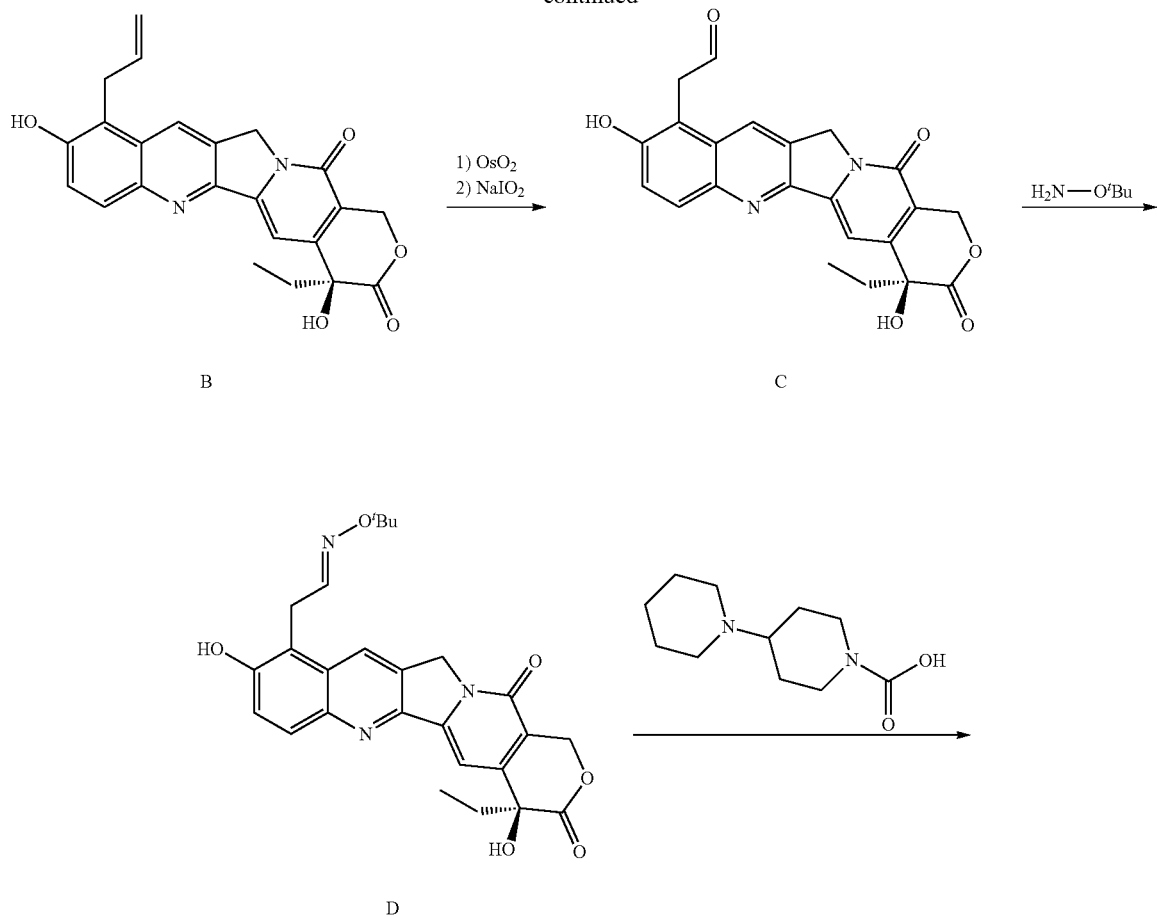

2. The Compounds and their Pharmaceutical Compositions

The invention also provides pharmaceutical compositions comprising an effective amount of the compounds of this invention, wherein said pharmaceutical compositions are administered orally or via injection.

Oral drugs can be in the form of tablets, capsules, oral solutions, granules, suspensions, etc. The excipients for the oral drugs are conventional pharmaceutical excipients comprising diluents, flavoring agents, solubilizers, lubricants, suspending agents, binders, bulking agents, etc.

Injection preparations can be in the form of liquid, powder, lyophilized powder, liposomes, etc. The excipients for the injection preparations are conventional pharmaceutical excipients comprising solvents, diluents, solubilizers, pH regulators, etc.

The effective amount refers to the dosage producing a positive therapeutic effect in a patient; the actual dosage depends on the route of drug administration and the dosing regimen.

3. Uses of the Compounds and their Compositions in the Treatment of Cancer

1) In vitro bioactivity of the novel camptothecin derivatives MTT assay was used to test the in vitro inhibitory effects of CPT1-CPT10, the active component of irinotecan (SN-38), gimatecan and topotecan against the A549 (non-small cell lung cancer), HT-29 (colon), OV-3 (ovarian cancer), U87 (glioma), BX-PC3 (pancreatic cancer) cell lines. The results showed that, among CPT1-10, the prodrugs CPT1, CPT4, CPT5, CPT6, CPT9 and CPT10 do not have significant activities in vitro (not recorded in the table) while CPT2, CPT3, CPT7 and CPT8 showed significant cytotoxicity.

The effects of CPT2, CPT3, CPT7, CPT8, gimatecan, SN-38 and topotecan on the above five cell lines ranked from strongest to weakest in the order U87, BX-PC3, HT-29, OV-3 and A549. The average concentrations (nM) of these compounds that inhibited 50% cell growth of U87, BX-PC3, HT-29, OV-3 and A549 were respectively: CPT7 (3.3), CPT3 (7.1), gimatecan (2.7), CPT2 (9.1), SN-38 (10.5), CPT8 (12.9), and topotecan (197). (See Table 1).

2) The therapeutic effect of the novel camptothecin derivatives on human tumor xenografts: In order to accurately evaluate the in vivo anti-tumor effects of the novel camptothecin derivatives, comparison of the anti-tumor effects had to be made at the same level of toxicity, and all the experiments were therefore conducted at the maximum tolerated dose (MTD). The experimentally determined dosages for these compounds to be at the same level of toxicity (decrease in weight of around 15%) were: CPT1 55 mg/kg, q2dx4; irinotecan 55 mg/kg, q2dx4; gimatecan 1 mg/kg, q2dx4; topotecan 12 mg/kg, q2dx4. CP1 had better solubility and stability than CPT2-10. The results showed that CPT1 had good therapeutic effect against a variety of transplanted tumors.

EXAMPLES

This invention will be further illustrated with the following examples which are not meant to limit the scope of this invention.

Example 1

Methods for Preparing CPT1

A. Synthesis of 10-allyloxy-camptothecin

To a 500 ml double-mouth flask equipped with an argon balloon were added 10.0 g (27.5 mmol) of 10-hydroxy-camptothecin and 200 ml of DMF. The mixture was stirred until all solids had fully dissolved, and then 5.6 g (4.0 mmol) of potassium carbonate and 2.6 ml (3 mmol) of allyl bromine were successively added and allowed to react at room temperature under argon.

After the reaction, the product was poured into 250 ml of ice water, and dilute hydrochloric acid was added to adjust the pH to 5. The yellow solids that precipitated were isolated by filtration followed by washing the filtered cake with 3×100 ml of water, and 100 ml of diethyl ether. Subsequent drying gave a pale yellow powder, 9.8 g (24.2 mmol) with a yield of 88.2%.

$^1$H NMR (CDCl$_3$): δ 8.21 (s, 1H), 8.12 (d, 1H), 7.62 (s, 1H), 7.48 (d, 1H), 7.14 (s: 1H), 6.11 (m, 1H), 5.73 (d, 1H), 5.50 (dd, 1H), 5.47 (dd, 1H), 5.30 (m, 1H), 5.25 (s, 2H), 4.71 (d, 2H), 3.88 (s, 1H), 1.76 (m, 2H), 1.03 (t, 3H).

B. Synthesis of 9-allyl-10-hydroxy-camptothecin

To a 1000 ml double-mouth flask equipped with an argon balloon and a reflux condenser were added 9.8 g (24.2 mmol) of 10-allyloxy-camptothecin and 500 ml of glacial acetic acid. The mixture was heated at reflux under argon for 3 days before it was evaporated to dryness under reduced pressure. Silica gel column chromatography with dichloromethane: methanol=30:1 (v/v) as eluent was used to give 6.4 g (15.8 mmol) of brown yellow powder, with a yield of 65.3%.

$^1$H NMR (DMSO-d6): δ 10.19 (s, 1H), 8.61 (s, 1H), 7.95 (d, 1H), 7.53 (d, 1H), 7.26 (s, 1H), 6.45 (s, 1H) 6.10 (m, 1H), 5.40 (s, 2H), 5.23 (s, 2H), 4.98 (m, 2H), 3.78 (d, 2H), 1.85 (m, 2H), 0.88 (t, 3H).

C. Synthesis of 2-(10-hydroxy-camptothecin-9-)acetaldehyde

To a 500 ml double-mouth flask were added 6.4 g (15.8 mmol) of 9-allyl-10-hydroxy-camptothecin, 250 ml dioxane and 80 ml water. The mixture was stirred until all solids had dissolved, and then 0.040 g (0.158 mmol) of osmium tetroxide was added. The mixture was stirred at room temperature for 30 minutes before 16.8 g (79.0 mmol) of sodium periodate were added portionwise within one hour. The reaction was stopped after 16 hours. An amount of 18.0 g of Na$_2$S$_2$O$_3$ was added. The mixture was stirred for half an hour before it was poured into 500 ml water, adjusted with dilute hydrochloric acid to pH=5, and extracted with chloroform (500 ml×6). The combined chloroform layer was washed with brine, and dried with anhydrous sodium sulfate. After Na$_2$SO$_4$ was removed by filtration, the solvent was distilled off under reduced pressure. Silica gel column chromatography with chloroform: acetone=10:1 (v/v) as eluent was used to obtain 3.1 g (7.6 mmol) of light yellow powder, with a yield of 48.1%.

$^1$H NMR (DMSO-d6): δ 9.79 (s, 1H), 8.68 (d, 1H), 7.88 (d, 1H), 7.82 (d, 1H), 7.38 (s, 1H), 6.47 (s, 1H), 5.41 (s, 2H), 5.36 (s, 2H), 5.23 (s, 2H), 4.32 (s, 2H), 1.88 (m, 2H), 0.87 (t, 3H).

D. Synthesis of 2-(10-hydroxy-camptothecin-9-)t-butylamino-oxime

To a 250 ml double-mouth flask equipped with an argon balloon and reflux condenser were added 3.1 g (7.6 mmol) of 2-(10-hydroxy-camptothecin-9-)acetaldehyde, 20 ml of ethanol, 1.9 g (15.2 mmol) of t-butylamine hydrochloride and 20 ml of pyridine. The mixture was stirred for 15 hours at 90° C. under argon. After the reaction was completed, the solvent was distilled off under reduced pressure, the residue was separated by silica gel column chromatography, with dichloromethane: methanol=30:1 (v/v) as eluent, to obtain 2.1 g (4.1 mmol) of pale yellow powder, a yield of 53.9%.

1H NMR δ 0.88 (t, H3-E+H3-Z), 1.28 (s, t-Bu Z) 1.41 (s, t-Bu E) 1.80-1.90 (m, H2-E+H2-Z), 4.32 (s, 2H), 5.10-5.40 (m, H2-E+H2-Z), 6.53 (s, OH), 7.25-7.50 (m, H-E+H-Z), 7.70 (d, H-E,) 8.05 (d, H-E+H-Z), 8.25 (s, Z), 9.0 (s, E) 10.35 (s, 1H).

1. Synthesis of 10-[(4'-piperidinylpiperidinyl)carbonyloxy]-9-t-butylamine-ethyloxime-camptothecin 1.5 g (6.5 mmol) of piperidinylpiperidinyl-chlorocarbonylamide was dissolved in 30 ml of dichloromethane. 2.1 g (4.4 mmol) of 2-(10-hydroxycamptothecin-9-)t-butylamine-oxime was dissolved in 30 ml of anhydrous pyridine, which was cooled in an ice bath while the aforementioned dichloromethane solution was added. The mixture was stirred for 16 hours at room temperature and, after the reaction was completed, the solvent was distilled off under reduced pressure. The residue was then purified by silica gel column chromatography to obtain 2.1 g of yellow solid, at a yield of 70.1%.

$^1$H NMR (CDCl$_3$): δ 8.78 (s, E), 8.61 (s, Z), 8.13 (d, 1H), 7.66 (d, 1H), 7.58 (dd, 1H), 7.37 (t, E), 6.68 (t, Z), 5.74 (d, 1H), 5.29 (d, 1H), 5.26 (s, 2H), 4.43 (br, 1H), 4.32 (d, 1H), 4.11 (d, Z), 3.93 (d, E), 3.1 (t, 1H), 2.95 (t, 1H), 2.57 (br, 4H), 1.95 (br, 2H) 1.83 (m, 2H), 1.63 (br, 4H), 1.47 (br, 2H), 1.27 (s, E), 1.25 (s, Z), 1.03 (t, 3H).

Example 2

Methods for Preparing CPT2-10

Methods for preparing CPT2-10 were the same as Example 1, and differed only in the starting materials which were compounds having the corresponding substituents.

Example 3

Preparation of Tablets Comprising CPT1

Formulation CPT1 50 g
Microcrystalline cellulose 100 g
Lactose 100 g
Starch 8 g
Magnesium stearate 30 g
Methyl cellulose 1 g
Formulated into 1000 tablets (50 mg/tablet).

Example 4

Preparation of Capsules Comprising CPT1

Formulation CPT1 50 g
Microcrystalline cellulose 200 g
Starch 250 g
Mixed and loaded into 1000 capsules at 50 mg/capsule.

Example 5

Preparation of Tablets and Capsules Comprising CPT2, CPT3

Same as Example 3 and Example 4

Example 6

In Vitro Cytotoxicity on Tumor Cells

In vitro cytotoxicity was measured with MTT. Cell suspension was prepared using cells in good condition and seeded at 200 μl/well on a 96 well plate before culturing for 24 hours in a temperature-controlled CO$_2$ incubator. The test drug was added at 20 μl/well and cultured for 48 hours. MTT was added to the 96 well plate at 20 ul/well and allowed to react for 4 hours in the incubator. The supernatant was removed and DMSO was added at 20 μl/well. Cytotoxicity was determined by the absorbance measured by Enzyme-linked immunosorbent assay at a wavelength of 570 nm.

TABLE 1

Inhibition effect of the novel camptothecin derivatives on tumor cells in vitro

| | Concentration to inhibit 50% cell growth (IC50 nM ± SD) | | | | | |
|---|---|---|---|---|---|---|
| Cell | A549 | HT-29 | OV-3 | U87 | BX-PC3 | mean |
| CPT2 | 14.1 ± 1.2 | 7.1 ± 1.6 | 16.1 ± 2.5 | 2.9 ± 1.1 | 5.1 ± 2.0 | 9.1 |
| CPT3 | 11.2 ± 1.0 | 9.1 ± 3.2 | 10.1 ± 2.1 | 2.1 ± 1.0 | 3.1 ± 1.5 | 7.1 |
| CPT7 | 5.5 ± 0.8 | 3.1 ± 1.0 | 4.1 ± 0.4 | 1.5 ± 0.3 | 2.1 ± 1.2 | 3.3 |
| CPT8 | 19.3 ± 2.2 | 11.1 ± 1.8 | 23.1 ± 3.1 | 4.1 ± 1.7 | 7.1 ± 2.1 | 12.9 |
| SN38 | 16.6 ± 1.9 | 8.7 ± 1.2 | 17.1 ± 3.2 | 3.1 ± 1.1 | 6.8 ± 2.6 | 10.5 |
| Gimatecan | 4.7 ± 0.2 | 3.6 ± 0.3 | 3.1 ± 2.2 | 0.6 ± 0.2 | 1.5 ± 0.8 | 2.7 |
| Topotecan | 28.5 ± 3.9 | 17.3 ± 4.2 | 21.1 ± 2.6 | 12.5 ± 3.2 | 19.1 ± 3.7 | 19.7 |

A549: non-small cell lung cancer, HT-29: colon cancer, OV-3: ovarian cancer, U87: glioma, BX-PC3: Pancreatic cancer The average concentrations (nM) of the above compounds showing 50% inhibition on cell growth of U87, BX-PC3, HT-29, OV-3, A549 were respectively: CPT7 (3.3), CPT3 (7.1), gimatecan (2.7), CPT2 (9.1), SN-38 (10.5), CPT8 (12.9), topotecan (19.7).

Example 6

In Vivo Anti-Tumor Effects

Methods: female nude mice were used for the experiments. Transplantation of tumors: Actively growing tumor tissues were cut into small pieces with sterilized scissors and each mouse was inoculated with 50 mg of the tumor tissue. Treatment began on days 6-10 after tumor transplantation when the weight of the tumor was around 300 mg. The nude mice were weighed and the tumor size was measured every other day. Transplanted tumors: human breast cancer (MX-1), human non-small cell lung cancer (A549), human ovarian carcinoma (SK-0V3), human colon carcinoma (HT29), human pancreatic cancer (BX-PC-3).

A:

$$\text{Inhibtory rate}(\%) = \frac{(\text{Tumor size in control group} - \text{Tumor size in treatment group})}{\text{Tumor size in control group}} \times 100\%$$

B: Tumor disappearance: tumor could not be detected visually 60 days after the experiment

TABLE 2

Therapeutic effect on the nude mouse with MX-1 human breast cancer xenograft

| Compound | Dose (mg/kg) | Number of animals Begin | Number of animals End | T.S. (mm3) D 0 | T.S. (mm3) D 16# | Tumor disappear | Maximum change in weight (%) |
|---|---|---|---|---|---|---|---|
| Control | Solvent | 6 | 6 | 312 ± 34 | 2100 ± 267 | 0/6 | +6% |
| CPT1 | 55 | 6 | 6 | 356 ± 51 | 0 | 6/6 | −13% |
| Topotecan | 10 | 6 | 6 | 323 ± 47 | 124 ± 12 | 2/6 | −14% |
| Irinotecan | 60 | 6 | 6 | 361 ± 54 | 0 | 6/6 | −12% |
| Gimatecan | 1 | 6 | 6 | 328 ± 65 | 0 | 6/6 | −13% |

Dosing regimen: once every two days, a total of four times; route of administration: intravenous injection at the tail vein. # At 16 days after treatment. The disappearance of tumor was observed for 60 days. The doses used were those that were determined experimentally to cause the same toxicity of weight decrease by 12-15%. T.S: tumor size

TABLE 3

Therapeutic effect on nude mice with SK-OV3 human ovarian carcinoma xenograft

| Compound | Dose (mg/kg) | Number of animals Begin | Number of animals End | T.S. (mm3) D 0 | T.S. (mm3) D 16# | Tumor inhibition | Maximum change in weight (%) |
|---|---|---|---|---|---|---|---|
| Control | Solvent | 6 | 6 | 211 ± 24 | 1823 ± 123 | 0 | +8% |
| CPT1 | 55 | 6 | 6 | 236 ± 34 | 358 ± 34 | 80.4 | −12% |
| Topotecan | 10 | 6 | 6 | 223 ± 43 | 1478 ± 226 | 18.9 | −12% |
| Irinotecan | 60 | 6 | 6 | 214 ± 26 | 451 ± 56 | 75.3 | −13% |
| Gimatecan | 1 | 6 | 6 | 203 ± 33 | 578 ± 61 | 68.4 | −12% |

Dosing regimen: once every two days, a total of four times; route of administration: intravenous injection at the tail vein. # At 16 days after treatment. The doses used were those that were determined experimentally to cause the same toxicity of weight decrease by 12-15%. T.S: tumor size

TABLE 4

Therapeutic effect on the intra-cerebrally transplanted U87 human glioma brain tumor

| Compound | Dose (mg/kg) | Number of animals Begin | Number of animals End | Average survival time (days) |
|---|---|---|---|---|
| Control | Solvent | 10 | 0 | 18.6 ± 1.3 |
| CPT1 | 55 | 10 | 0 | 26.4 ± 1.2# |
| Irinotecan | 60 | 10 | 0 | 22.8 ± 1.4 |
| Gimatecan | 1 | 10 | 0 | 23.1 ± 1.6 |

Dosing regimen: once every two days, a total of four times; route of administration: intravenous injection at the tail vein. Mice died from brain tumor after inoculation with $2\times10^5$ cells. #: Comparing CPT1 with irinotecan and gimatecan. Survival time increased significantly, P<0.05.

What is claimed is:

1. A compound or a pharmaceutically acceptable salt thereof, wherein said compound is selected from the group consisting of:
    CPT1: 9-t-butyloxyethyloxime-10-[(4'-piperidinylpiperidinyl)carbonyloxy]-camptothecin,
    CPT2: 9-t-butyloxyethyloxime-10-hydroxy-camptothecin,
    CPT3: 9-t-butyloxyethyloxime-10-fluoro-camptothecin,
    CPT7: 9-t-butyloxyethyloxime-camptothecin, and
    CPT8: 9-t-butyloxyethyloxime-10-acetoxyl-camptothecin.

2. The compound or pharmaceutically acceptable salt thereof of claim 1, wherein said salt is selected from hydrochloride, hydrobromide, phosphate, sulfate, acetate, trifluoroacetate, citrate, maleate, oxalate, succinate, benzoate, tartrate, fumarate, mandelate, ascorbate, malate, methanesulfonate, and p-toluenesulfonate.

3. A pharmaceutical composition comprising an effective amount of the compound or pharmaceutically acceptable salt thereof of claim 1, and any conventional pharmaceutical excipients.

4. The pharmaceutical composition of claim 3, formulated for oral administration or injection.

5. A method for treating tumor in a subject, comprising administering to the subject an effective amount of the compound or pharmaceutically acceptable salt thereof of claim 1, wherein said tumor is selected from ovary cancer, glioma, pancreatic cancer, colon cancer and non-small cell lung cancer.

\* \* \* \* \*